(12) United States Patent
Uchida et al.

(10) Patent No.: US 9,238,025 B2
(45) Date of Patent: Jan. 19, 2016

(54) TRANSDERMAL PREPARATION COMPRISING A ROPINIROLE DERIVATIVE

(75) Inventors: Naoyuki Uchida, Tsukuba (JP); Yuka Takagi, Tsukuba (JP); Yasunori Takada, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 612 days.

(21) Appl. No.: 13/319,401

(22) PCT Filed: May 7, 2010

(86) PCT No.: PCT/JP2010/057807
§ 371 (c)(1),
(2), (4) Date: Nov. 8, 2011

(87) PCT Pub. No.: WO2010/134433
PCT Pub. Date: Nov. 25, 2010

(65) Prior Publication Data
US 2012/0052113 A1  Mar. 1, 2012

(30) Foreign Application Priority Data
May 21, 2009 (JP) ................................ P2009-123429

(51) Int. Cl.
| | |
|---|---|
| *A61K 9/70* | (2006.01) |
| *A61K 31/404* | (2006.01) |
| *A61K 31/4045* | (2006.01) |
| *A61P 25/16* | (2006.01) |
| *A61K 45/06* | (2006.01) |

(52) U.S. Cl.
CPC ............. *A61K 31/404* (2013.01); *A61K 9/7038* (2013.01); *A61K 31/4045* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,452,808 A | 6/1984 | Gallagher, Jr. | |
| 5,807,570 A | 9/1998 | Chen et al. | |
| 7,175,853 B1 * | 2/2007 | Bracht | ........................ 424/449 |

FOREIGN PATENT DOCUMENTS

| | | |
|---|---|---|
| EP | 0300614 A1 | 1/1989 |
| JP | 59-112964 A | 6/1984 |
| JP | 64-19065 A | 1/1989 |
| JP | 01-190658 A | 7/1989 |
| JP | 11-506462 A | 6/1999 |
| JP | 2001-518058 A | 10/2001 |
| JP | 2004-331500 A | 11/2004 |
| JP | 2005-23088 A | 1/2005 |
| JP | 2007-176880 A | 7/2007 |
| JP | 2008-239497 A | 10/2008 |
| WO | 96/39136 A1 | 12/1996 |
| WO | 2005/105741 A1 | 11/2005 |
| WO | 2008/069283 A1 | 6/2008 |
| WO | 2009/107478 A1 | 9/2009 |
| WO | 2009/107479 A1 | 9/2009 |
| WO | 2010/123103 A1 | 10/2010 |

OTHER PUBLICATIONS

Official Action issued Sep. 28, 2012 for counterpart Chinese patent application No. 201080013234.x.
Search Report issued in European Patent Application No. 10777667.6 dated Dec. 20, 2013, 4 pages.
Hayler, J.D., et al, Some synthetic approaches to ropinirole (SK&F 101468-A) : a potent dopamine receptor agonist, Journal of Heterocyclic Chemistry, 1995, vol. 32, No. 3, p. 875-882.
International Search Report for corresponding International Application PCT/JP2010/057807, completed May 31, 2010, mailed Jun. 8, 2010, two pages.
English Translation of the International Preliminary Report on Patentability for corresponding International Application No. PCT/JP2010/057807, mailed on Dec. 22, 2011, seven pages.

* cited by examiner

*Primary Examiner* — Kevin S Orwig

(74) *Attorney, Agent, or Firm* — Nath, Goldberg & Meyer; Joshua B. Goldberg; Tanya E. Harkins

(57) ABSTRACT

The present invention relates to a transdermal preparation having a backing and an adhesive layer laminated on the backing, wherein the adhesive layer contains 4-ethylene-2(3H)-indolone and a physiologically active compound, and wherein the 4-ethylene-2(3H)-indolone is present in an amount from 0.001 to 4 mass % of the total mass of components of the adhesive layer.

1 Claim, No Drawings

TRANSDERMAL PREPARATION COMPRISING A ROPINIROLE DERIVATIVE

TECHNICAL FIELD

The present invention relates to a transdermal preparation.

BACKGROUND ART

Ropinirole is provided as oral preparations in the form of hydrochloric acid addition salts, and used for the treatment of Parkinson's disease. Patent Literatures 1 and 2 each describe the inventions relating to the production processes of ropinirole as a drug substance and high purity ropinirole hydrochloride as a drug substance. Also, transdermal preparations containing ropinirole are disclosed in, for example, Patent Literatures 3 and 4. Patent Literature 5 describes that, in a transdermal drug delivery system, the liquid body and the basic form of low-molecular weight drugs exhibits excessive plasticizing effects on a polymer.

Meanwhile, 4-ethylene-2(3H)-indolone having the following molecular structure (alternative name: 4-ethylenyl-1,3-dihydro-2H-indol-2-one. Hereinbelow, this compound may be abbreviated as "4E indolone") is given a CAS No. 120427-93-2, and known as a decomposition product of ropinirole N-oxide.

[Chemical Formula 1]

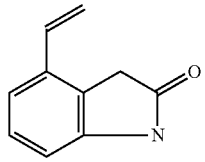

CITATION LIST

Patent Literature

Patent Literature 1: WO2005/105741
Patent Literature 2: JP-A-59-112964
Patent Literature 3: JP-T-11-506462
Patent Literature 4: JP-T-2001-518058
Patent Literature 5: JP-A-2005-023088

SUMMARY OF INVENTION

Technical Problem

Because transdermal preparations are stuck to the skin and the like upon application, a suitable tackiness is required, while it is important that they have a sufficient transdermal absorption property of physiologically active compounds. Meanwhile, 4E indolone having the aforementioned molecular structure is known as the decomposition product of ropinirole, but its special usage is not known.

In view of the above, an object of the present invention is to provide a transdermal preparation having a suitable tackiness and a sufficient transdermal absorption property of physiologically active compounds through effective utilization of 4E indolone.

Solution to Problem

In view of the foregoing, the present inventors conducted intensive research. As a result, they found that when 4E indolone was contained in an adhesive layer of a transdermal preparation, 4E indolone exerted an excellent plasticizing action on the adhesive layer of the transdermal preparation. They also found that even when the aforementioned adhesive layer contained ropinirole, the transdermal preparation could maintain a sufficient transdermal absorption property of physiologically active compounds. Based on the above findings, they accomplished the present invention.

That is, the present invention provides a transdermal preparation comprising a backing and an adhesive layer laminated on the backing, wherein the adhesive layer comprises 4E indolone and a physiologically active compound.

As the physiologically active compound, indole derivatives or pharmaceutically acceptable acid addition salts thereof can be applied. In this case, ropinirole is preferable as the indole derivative, and ropinirole hydrochloride is preferable as the pharmaceutically acceptable acid addition salt.

Advantageous Effects of Invention

In a transdermal preparation, plasticity and tackiness of an adhesive layer are improved by inclusion of 4E indolone in the adhesive layer, and even when the adhesive layer contains ropinirole, a 4E indolone-containing transdermal preparation capable of maintaining a sufficient transdermal absorption property of physiologically active compounds can be provided.

DESCRIPTION OF EMBODIMENTS

The transdermal preparation of the present invention is a transdermal preparation comprising a backing and an adhesive layer laminated on the backing, wherein the adhesive layer comprises at least a physiologically active compound, 4E indolone, and an adhesive base.

The backing may be a material onto which an adhesive layer can be laminated, and either a stretchy or non-stretchy material can be used. As the backing, one made of a material that does not swell due to the components of the adhesive layer is preferable. Specifically, films, porous membranes, foam sheets, cloth, and the like formed by a material such as polyester (such as polyethylene terephthalate, polyethylene naphthalate, and polybutylene terephthalate), polyolefin (such as polyethylene and polypropylene), rubber (such as polyisoprene, polybutadiene, and SIS), ethylene vinyl acetate polymers, polyvinyl chloride, polyacrylonitrile, nylon, polyurethane, cellulose derivatives, and metallic foils (such as aluminum) can be preferably used.

The physiologically active compound is a compound producing, when the transdermal preparation of the present invention is applied to a human, a therapeutic effect and the like by exerting physiological activities via transdermal absorption. As the physiologically active compound, a physiologically active compound having an indole structure is preferable.

Examples of the physiologically active compound having an indole structure include indole derivatives such as indomethacin, etodolac, sumatriptan, rizatriptan, ropinirole, [3-[(2R)-[[(2R)-(3-chlorophenyl)-2-hydroxyethyl]amino]propyl]-1H-indol-7-yloxy]acetic acid, 3-(2-aminopropyl)indole, pindolol and ramosetron, and pharmaceutically acceptable acid addition salts of these indole derivatives.

Although examples of the pharmaceutically acceptable acid addition salts of the indole derivatives include acid addition salts of indole derivatives with hydrochloric acid, citric acid, acetic acid, fumaric acid, lactic acid, maleic acid, sulfuric acid, tartaric acid, mesylic acid, and the like, no particular limitation is imposed thereon.

As the pharmaceutically acceptable acid addition salt of the indole derivative, ropinirole hydrochloride, which has similar molecular structure and physicochemical characteristics to 4E indolone, is particularly preferable.

The 4E indolone is contained in such an amount that does not adversely affect the therapeutic effect and the like of the physiologically active compounds, and the content is preferably 0.001 to 4 mass % of the total mass of the components of the adhesive layer.

The 4E indolone may be an acid addition salt of 4E indolone with hydrochloric acid, citric acid, acetic acid, fumaric acid, lactic acid, maleic acid, sulfuric acid, tartaric acid, mesylic acid, and the like.

Although an adhesive base is not particularly limited as long as it is an adhesive base having excellent tackiness and drug-releasing properties, acrylic adhesive bases, rubber bases, silicone adhesive bases, and the like are preferably used. Among these, particularly, a (meth)acrylic acid ester copolymer, which is a polymer containing a (meth)acrylic acid ester as a monomer unit, a styrene block copolymer containing a styrene block as a hard segment, or an adhesive base containing the aforementioned (meth)acrylic acid ester adhesive base and the block copolymer can be preferably used.

Although the acrylic adhesive base is not particularly limited as long as it is a polymer containing at least acrylic acid or one (meth)acrylic acid (ester) such as, 2-ethylhexyl acrylate, methyl acrylate, butyl acrylate, hydroxyethyl acrylate, 2-ethylhexyl methacrylate or the like as a monomer. Examples thereof include 2-ethylhexyl acrylate/vinyl acetate copolymers, 2-ethylhexyl acrylate/vinyl acetate/acrylic acid copolymers, 2-ethylhexyl acrylate/vinyl acetate/hydroxyethyl acrylate copolymers, 2-ethylhexyl acrylate/vinyl acetate/hydroxyethyl acrylate/acrylic acid copolymers, and 2-ethylhexyl acrylate/2-ethylhexyl methacrylate/dodecyl methacrylate copolymers, among which, particularly, 2-ethylhexyl acrylate/vinyl acetate copolymers and 2-ethylhexyl acrylate/vinyl acetate/acrylic acid copolymers are preferable.

Examples of the rubber base include styrene block copolymers, polyisoprene, polybutadiene, polyvinyl acetate, ethylene.vinyl acetate copolymers and natural rubber, and particularly, styrene block copolymers can be preferably used.

Examples of the styrene block copolymer include styrene-isoprene-styrene block copolymers (SIS), styrene-butadiene-styrene block copolymer (SBS), styrene-ethylene.butylene-styrene block copolymers (SEBS) and styrene-ethylene.propylene-styrene block copolymers (SEPS), and particularly, SIS is preferable.

An adhesive base in which an acrylic adhesive base such as a 2-ethylhexyl acrylate/vinyl acetate/acrylic acid copolymer and a styrene block copolymer such as SIS are mixed is also usable.

As the silicone adhesive base, one that is mainly composed of polyorganosiloxane such as polydimethylsiloxane and contains a tackifier such as MQ resin is usable.

The adhesive layer can contain other ingredients such as desalting agents, softeners, tackifiers, absorption promoters or solubilizers, stabilizers and fillers, as needed.

The desalting agent is a substance that removes salts from physiologically active compounds in the form of acid addition salts to generate free physiologically active compounds. Sodium hydroxide, potassium hydroxide, magnesium hydroxide and the like can be used, and particularly, sodium hydroxide is preferably used.

The blending ratio of the desalting agent is preferably within a range of 0.2 to 3 times the mole number of the acid to be added to the physiologically active compounds, and it is more preferably equimolar to the acid to be added to the physiologically active compounds.

Examples of the softener include liquid paraffin, vegetable oil (such as almond oil, olive oil, camellia oil, castor oil, tall oil, and peanut oil), animal oil (such as squalane and squalene), fatty acid, fatty acid esters (such as isopropyl myristate, hexyl laurate, diethyl sebacate, or isopropyl sebacate), liquid rubbers (such as liquid polybutene and liquid polyisoprene), aliphatic alcohols, glycols (diethylene glycol, polyethylene glycol, propylene glycol, and dipropylene glycol), triacetin, triethyl citrate, and crotamiton. Among them, particularly, liquid paraffin, isopropyl myristate and diethyl sebacate are preferable because they can provide an appropriate adhesion to the skin. One kind of these softeners may be used alone or two or more kinds thereof may be used in combination.

Examples of the tackifier include alicyclic saturated hydrocarbon resins, rosin derivatives (such as rosin, glycerin esters of rosin, hydrogenated rosin, hydrogenated rosin glycerin esters, rosin pentaerythritol esters and hydrogenated rosin pentaerythritol esters), terpene resins, petroleum resins or maleic acid resins. Among them, particularly, alicyclic saturated hydrocarbon resin and hydrogenated rosin glycerin esters are preferable. One of these tackifiers may be used alone or two or more thereof may be used in combination.

Examples of the absorption promoter or solubilizer can include aliphatic alcohols (such as octyldodecanol and isostearyl alcohol), fatty acids (such as oleic acid and capric acid), fatty acid derivatives (such as isopropyl myristate, isopropyl palmitate, propylene glycol laurate and lauric acid diethanolamide), glycols (such as propylene glycol and polyethylene glycol), N-alkyl pyrrolidone and acetic acid.

Further, in order to inhibit precipitation of drug crystals, polyvinylpyrrolidone, crospovidone, aminoalkylmethacrylate copolymer E, aminoalkylmethacrylate copolymer RS, methacrylic acid copolymer L, methacrylic acid copolymer S, methacrylic acid copolymer LD, polyvinylacetal diethylaminoacetate, and the like can also be used.

One of these absorption promoters or solubilizers may be used alone or two or more thereof may be used in combination.

In consideration of sufficient permeability of the active ingredient into the tissues, local stimulation, and the like of a preparation, the blending ratio of the absorption promoter is preferably 1 to 50 mass %, more preferably 3 to 15 mass % of the total mass of the components of the adhesive layer.

Examples of the stabilizer can include antioxidants (such as tocopherol derivatives, ascorbic acid derivatives, erythorbic acid derivatives, nordihydroguaiaretic acid, gallic acid derivatives, dibutylhydroxytoluene, butylhydroxyanisole, sodium pyrosulfite and sodium sulfite) and ultraviolet absorbers (such as imidazole derivatives, benzotriazole derivatives, p-aminobenzoic acid derivatives, anthranilic acid derivatives, salicylic acid derivatives, cinnamic acid derivatives, benzophenone derivatives, coumaric acid derivatives and camphor derivatives).

Examples of the filler can include metal oxides (such as zinc oxide and titanium oxide), metal salts (such as calcium carbonate, magnesium carbonate and zinc stearate), silicic acid compounds (such as kaolin, talc, bentonite, Aerosil, hydrous silica, aluminum silicate, magnesium silicate and magnesium aluminometasilicate) and metal hydroxides (such as aluminum hydroxide).

The transdermal preparation of the present invention can have a release liner to cover and protect the adhesive layer.

As the release liner, a film of, for example, polyester (such as polyethylene terephthalate, polyethylene naphthalate and polybutylene terephthalate) and polyolefin (such as polyethylene and polypropylene), paper, and the like can be used, and one having been subjected to releasing treatment by coating a side in contact with the adhesive layer with silicone, Teflon (registered trademark), and the like is preferable, and particularly, a silicone-treated polyethylene terephthalate film is preferably used.

Although the production method of the transdermal preparation of the present invention is not particularly limited, for example, a transdermal preparation can be obtained by melting each component of the adhesive layer, such as the physiologically active compound, 4E indolone and the adhesive base, with heat and applying the melted product to a release liner or a backing to form an adhesive layer, and then sticking the adhesive layer thus obtained to a release liner or a backing.

Also, a transdermal preparation can be obtained by dissolving each component of the composition of the adhesive layer, such as the physiologically active compound, 4E indolone and the adhesive base, in an organic solvent (such as toluene, hexane, heptane and ethyl acetate) and the like to give a solution, and after applying it to a release liner, removing the solvent component by drying to form an adhesive layer, and then sticking a backing to the adhesive layer thus obtained.

Although the packaging method of the transdermal preparation of the present invention is not particularly limited, it is preferably packaged in an aluminum laminated bag composed of a multilayer film laminate in which a sealant layer is composed of polyacrylonitrile.

EXAMPLES

Examples and Comparative Example

In accordance with the compositions shown in Table 1, transdermal preparations were prepared by the following procedures.

A mixed solution of ropinirole hydrochloride, 4E indolone, sodium hydroxide, liquid paraffin and toluene (solvent), and a separately prepared mixed solution of SIS, alicyclic hydrocarbon resin and toluene (solvent), were mixed to homogeneity to give an application liquid.

The application liquid thus prepared was spread over a polyethylene terephthalate film having been subjected to releasing treatment, and the resulting product was exposed to warm wind to remove the solvent component to form an adhesive layer, and subsequently, the resulting adhesive layer was covered with a backing composed of a polyethylene terephthalate film to give a laminate, and the laminate thus obtained was appropriately cut to give transdermal preparations, which were packaged in an aluminum laminated packaging material.

TABLE 1

| Component (mass %) | Comparative Example | Example 1 | Example 2 |
|---|---|---|---|
| Ropinirole hydrochloride | 5.00 | 4.99 | 4.98 |
| 4E Indolone | — | 0.01 | 0.02 |
| Sodium hydroxide | 0.5 | 0.5 | 0.5 |
| Liquid paraffin | 21.6 | 21.6 | 21.6 |
| SIS | 27.0 | 27.0 | 27.0 |
| Alicyclic saturated hydrocarbon resin | 45.9 | 45.9 | 45.9 |

TABLE 1-continued (Evaluation Test)

With regard to each of the transdermal preparations produced in Examples and Comparative Example, plasticity and tackiness were evaluated by an organoleptic test and a probe tack test, respectively, and the transdermal absorption property of the physiologically active compound was evaluated by a skin permeation test.

<Organoleptic Test Method>

Evaluation of plasticity: the plasticity of the adhesive layer was evaluated using the physical property of the adhesive as an index (finger tack).

<Probe Tack Test Method>

Evaluation of tackiness: with regard to the tackiness of the adhesive layer, each preparation was cut into 1 cm squares and served as a sample, and the adhesion strength value (gf) was measured using a probe tack tester (manufactured by Rigaku Kogyo) in accordance with a probe tack test method as defined in ASTM D2979 under the conditions of a contact speed of 1 mm/sec, a contact time of 1 second, a load of 20 g, with a probe made of Bakelite having a diameter of 5 mm$\phi$, and a release speed of 1 mm/sec.

<Skin Permeation Test Method>

Evaluation of transdermal absorption property: the transdermal absorption property of the physiologically active compounds was evaluated by a skin permeation test using hairless mouse skin in vitro.

In the test, firstly, the back skin of a hairless mouse was peeled off and set in a 5 square cm Franz flow-through cell with its dermal side facing the receptor layer side, while circulating warm water of 32° C. around the outer periphery of the cell. The sample was stuck to the stratum corneum side of the aforementioned skin, and phosphate buffered saline (PBS) of pH 7.4 was allowed to flow in the receptor layer, and the solution in the receptor layer was collected every two hours up to 24 hours.

The concentration of the physiologically active compounds in each collected solution was quantitated by high-performance liquid chromatography to obtain the amount of physiologically active compounds permeated across the skin per collection time, whereby the maximum permeation rate ($\mu g/cm^2/hr$) of the physiologically active compounds was obtained.

Also, the rate of utilization (%) was obtained by calculating the cumulative amount of physiologically active compounds permeated across the skin up to 24 hours and dividing the resulting value by the amount of physiologically active compounds added to 5 square cm transdermal preparations.

<Results of Evaluation>

As a result of the organoleptic test, in Examples in which the adhesive layer contained 4E indolone, the transdermal preparations exhibited good plasticity, whereas in Comparative Example in which 4E indolone was not contained, the transdermal preparation did not exhibit preferable plasticity.

Subsequently, the results of evaluation of the tackiness and transdermal absorption property are shown in Table 2. According to the probe tack test, in Examples in which the adhesive layer contained 4E indolone, the transdermal preparations exhibited a good tackiness, whereas in Comparative Example in which 4E indolone was not contained, the transdermal preparation did not exhibit a preferable tackiness.

As a result, with regard to the physical property of the adhesive, Examples 1 and 2 were superior to Comparative Example.

Also, according to the skin permeation test, it was found that even when the adhesive layer contained 4E indolone, a sufficient transdermal absorption property of the physiologically active compounds, that is, the maximum permeation rate and the rate of utilization were maintained.

TABLE 2

|  | Tackiness Adhesion strength (gf) | Transdermal absorption property | |
| --- | --- | --- | --- |
|  |  | Maximum permeation rate ($\mu g/cm^2/hr$) | Rate of utilization (%) |
| Comparative Example | 190 | 50.3 | 67.8 |
| Example 1 | 201 | 51.4 | 68.4 |
| Example 2 | 214 | 47.1 | 65.3 |

The invention claimed is:

1. A transdermal preparation comprising a backing and an adhesive layer laminated on the backing,
   wherein the adhesive layer contains 4-ethylene-2(3H)-indolone and a physiologically active compound, wherein the physiologically active compound is ropinirole hydrochloride, and wherein the 4-ethylene-2(3H)-indolone is present in an amount from 0.01 to 4 mass % of the total mass of components of the adhesive layer.

* * * * *